United States Patent [19]

Wedemeyer et al.

[11] 4,429,156

[45] Jan. 31, 1984

[54] PROCESS FOR THE PREPARATION OF M-HALOGEN-SUBSTITUTED ANILINES

[75] Inventors: Karlfried Wedemeyer, Cologne; Ferdinand Hagedorn, Leverkusen; Werner Evertz, Monheim, all of Fed. Rep. of Germany

[73] Assignee: Bayer Aktiengesellschaft, Leverkusen, Fed. Rep. of Germany

[21] Appl. No.: 313,905

[22] Filed: Oct. 22, 1981

[30] Foreign Application Priority Data

Nov. 8, 1980 [DE] Fed. Rep. of Germany ....... 3042242

[51] Int. Cl.$^3$ ............................................ C07C 85/24
[52] U.S. Cl. .................................. 564/412; 564/335; 564/374; 564/384
[58] Field of Search ................ 564/335, 374, 384, 412

[56] References Cited

U.S. PATENT DOCUMENTS

| 3,912,783 | 10/1975 | Wedemeyer et al. | 564/390 X |
| 4,193,937 | 3/1980 | Wedemeyer et al. | 564/305 |
| 4,351,959 | 9/1982 | Cordier | 564/412 |

FOREIGN PATENT DOCUMENTS

| 15219 | 3/1980 | European Pat. Off. | 564/335 |
| 2441650 | 3/1975 | Fed. Rep. of Germany . | |
| 2549900 | 5/1977 | Fed. Rep. of Germany . | |

*Primary Examiner*—Robert V. Hines
*Attorney, Agent, or Firm*—Sprung, Horn, Kramer & Woods

[57] ABSTRACT

An improved process for the preparation of an m-halogen-substituted aniline from a polyhalogen substituted aniline by the reaction of the aniline with hydrogen in an acid medium is disclosed wherein the process is carried out in the presence of hydrogen iodide and/or a compound which under the reaction conditions yields hydrogen iodide and in the presence of an optionally substituted phenol.

25 Claims, No Drawings

PROCESS FOR THE PREPARATION OF M-HALOGEN-SUBSTITUTED ANILINES

The invention relates to a process for the preparation of m-halogen-substituted anilines by selective dehalogenation of more highly halogenated anilines.

The preparation of m-chloro-substituted anilines by selective dehalogenation of more highly halogenated anilines in acid or neutral medium, in the presence of noble metal catalysts and, if appropriate, in the presence of sulphur and/or sulphur compounds, is known from German Pat. Nos. 2,503,145 and 2,503,187.

The processes described in German Pat. Nos. 2,503,145 and 2,503,187 only work economically, however, at high temperatures and pressures, that is to say at temperatures of over 200° C. and pressures of over 60 bars (in this respect, also compare the Examples of the patents). The technical application of these processes is made difficult by the fact, for example, that the high reaction temperatures and pressures employed place a particularly high stress on the container materials.

Furthermore, a process for the preparation of m-chloro-substituted anilines, in which the hydrogenating dehalogenation process is carried out in the presence of a greatly increased chloride ion concentration, is known from German Offenlegungsschrift No. 3,003,960. This process has the disadvantage that only small concentrations of the compound to be dehalogenated, in solutions with relatively high chloride ion concentration, can be used, leading to poor space-time yields and to increased corrosion of the apparatus. It can be assumed from the only Example of this Application that good results are only obtained in the presence of lithium chloride. In this procedure, however, large amounts of salt mixtures which are not separable are obtained, the processing and removal of which create particular ecological problems.

In the European Patent Application No. 0,015,219, a process is claimed in which the catalytically hydrogenating dehalogenation process is carried out in the presence of iodide ions or bromide ions. This process has the disadvantage that, in addition to the hydrogen chloride formed during the reaction, relatively large amounts of hydrochloric acid must be added, whereby, on the one hand, an increased amount of hydrogen chloride, or of the salt formed therefrom by neutralization, is formed of necessity, and, on the other hand, the risk of corrosion of the apparatus used is increased. A further substantial disadvantage is that only small concentrations of the compound to be dehalogenated can be employed in the reaction mixture (compare Examples 1 to 15; maximum 3% by weight). However, if larger amounts of starting material are to be dehalogenated, it is necessary to employ a large amount of catalyst, relative to the compound to be dehalogenated (compare Example 16; concentration of tetrachloronitrobenzene in the mixture: 12%, amount of catalyst: 57% by weight, relative to the tetrachloronitrobenzene). According to the above embodiments, the process described in the European Patent Application No. 0,015,219 is a process which is little suitable from a technical and economical viewpoint.

A process for the preparation of metahalogen-substituted anilines has now been found, in which anilines of the formula (I)

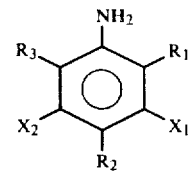

in which
X$_1$ and X$_2$ are identical or different and represent chlorine, bromine, iodine, hydrogen or an optionally substituted alkyl, aryl, aralkyl, alkoxy or aralkoxy radical, one of the radicals
X$_1$ or X$_2$ representing chlorine, bromine or iodine in the preparation of anilines substituted in a m-position by halogen, and X$_1$ and X$_2$ representing chlorine, bromine or iodine in the preparation of 3,5-dihalogeno-substituted anilines,
R$_1$, R$_2$ and R$_3$ are identical or different and represent chlorine, bromine, iodine, hydrogen or an optionally substituted alkyl, aryl, aralkyl, alkoxy or aryloxy radical, at least one of the radicals R$_1$, R$_2$ or R$_3$ representing chlorine, bromine or iodine, are reacted with hydrogen in an acid medium in the presence of a noble metal which can be, if desired, disposed on a carrier and is in elementary or bonded form, and if desired, in the presence of an inert organic solvent and/or diluent and/or water, at an elevated temperature and elevated pressure. The process is characterized in that the reaction is carried out in the presence of hydrogen iodide and/or a compound yielding hydrogen iodide under the process conditions. Optionally substituted phenols are simultaneously present.

According to the process according to the invention, m-halogen-substituted anilines of the formula (II) are obtained,

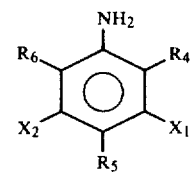

wherein
X$_1$ and X$_2$ have the meaning given above, and
R$_4$, R$_5$ and R$_6$ are identical or different and represent hydrogen or an optionally substituted alkyl, aryl, aralkyl, alkoxy or aryloxy radical.

Optionally substituted aliphatic radicals (R$_1$, R$_2$, R$_3$, R$_4$, R$_5$ and R$_6$) can be straight-chain or branched aliphatic radicals with 1 to 12, preferably with 1 to 6, carbon atoms, and cycloaliphatic radicals with 5 to 8, preferably 5 and 6, carbon atoms in the ring. Examples which may be mentioned are the methyl, the ethyl, the propyl, the isopropyl, the butyl, the pentyl, the hexyl, the octyl, the nonyl, the decyl, the dodecyl, the cyclopentyl, the cyclohexyl, the cycloheptyl and the cyclooctyl radicals.

Optionally substituted aromatic radicals (R$_1$, R$_2$, R$_3$, R$_4$, R$_5$ and R$_6$) can be radicals from the benzene series, preferably the phenyl or the naphthyl radical.

Optionally substituted aralkyl radicals (R$_1$, R$_2$, R$_3$, R$_4$, R$_5$ and R$_6$) can be those with 7 to 18 carbon atoms, the aliphatic part of which contains 1 to 6 carbon atoms, preferably 1 to 3 carbon atoms, and the aromatic part of which represents a radical of the benzene series, preferably the phenyl or the naphthyl radical. The following aralkyl radicals are mentioned as examples: the benzyl, the m-ethyl-phenyl, the γ-propyl-phenyl, the β-phenyl-n-hexyl, the β-[naphth-1-yl]-ethyl, the ω-butylphenyl, the ω-pentyl-phenyl and the ω-hexyl-phenyl radical.

Optionally substituted alkoxy radicals ($R_1$, $R_2$, $R_3$, $R_4$, $R_5$ and $R_6$) can be represented by straight-chain and branched radicals with 1 to 12, preferably with 1 to 6, carbon atoms, as well as by cycloaliphatic radicals with 5 to 6 carbon atoms in the ring. Examples which may be mentioned are the methoxy, the ethoxy, the propoxy, the isopropoxy, the butoxy, the tert.-butoxy, the pentoxy, the hexoxy, the oxy, the nonoxy, the decoxy, the dodecoxy, the cyclopentoxy and the cyclohexoxy radicals.

Optionally substituted aryloxy radicals ($R_1$, $R_2$, $R_3$, $R_4$, $R_5$ and $R_6$) which may be mentioned are radicals from the benzene series, preferably the phenoxy radical.

Suitable substituents of the alkyl, aryl, aralkyl, alkoxy or aralkoxy radicals listed above are, for example, the amino group, the hydroxyl group, straight-chain or branched alkyl radicals with up to 12, preferably up to 6, carbon atoms, cycloaliphatic radicals, preferably with 5 and 6 carbon atoms in the ring, and aryl radicals, preferably the phenyl radical.

Anilines which can be preferably employed in the process according to the invention are compounds of the formula (III)

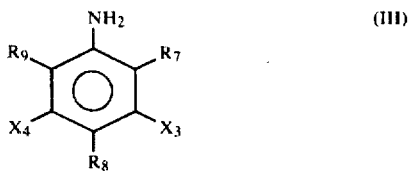

wherein
$X_3$ and $X_4$ are identical or different and represent chlorine, bromine, iodine or hydrogen, one of the radicals $X_3$ or $X_4$ representing chlorine, bromine or iodine in the preparation of 3-halogenoanilines, and $X_3$ and $X_4$ representing chlorine, bromine or iodine in the preparation of 3,5-dihalogenoanilines, $R_7$, $R_8$ and $R_9$ are identical or different and represent chlorine, hydrogen, the methyl group, the phenyl group or the radical

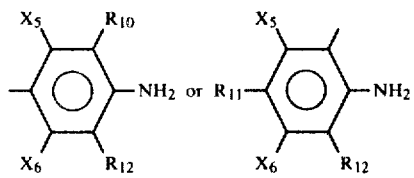

wherein
$X_5$ and $X_6$ are identical or different and represent chlorine, bromine, iodine or hydrogen,
$R_{10}$, $R_{11}$ and $R_{12}$ are identical or different and represent chlorine, hydrogen, the methyl group or the phenyl group, whereby at least one of the radicals $R_7$, $R_8$ or $R_9$ represents chlorine, bromine or iodine.

The polyhalogenoanilines of the formula (I) which can be used in the process according to the invention are known and easily obtainable. Examples which may be mentioned are: 2,3-dichloro-aniline, 2,5-dichloroaniline, 3,4-dichloro-aniline, 2,3,4-trichloro-aniline, 2,3,5-trichloro-aniline, 2,4,5-trichloro-aniline, 2,3,6-trichloro-aniline, 3,4,5-trichloro-aniline, 2,3,4,6-tetrachloro-aniline, 2,3,4,5-tetrachloro-aniline, 2,3,5,6-tetrachloro-aniline, pentachloro-aniline, 3-chloro-4-bromo-5-iodo-aniline, 4,5,6-trichloro-2-methyl-aniline, 2,5-dichloro-4-methyl-aniline, 2,3,5,6-tetrachloro-4-methyl-aniline, 2,5-dichloro-3,4-dimethyl-aniline, 2,5-dichloro-4-ethyl-aniline, 2,5-dichloro-4-propyl-aniline, 3,4,6-trichloro-2-benzyl-aniline, 2,2'-diamino-3,5,6,3',5',6'-hexachloro-diphenyl-methane, 3,4,5-trichloro-2-amino-diphenyl, 4,4'-diamino-octachlorodiphenyl, 3,4-dichloro-2-methoxy-aniline, 3,6-dichloro-2-methoxy-aniline, 4,5-dichloro-2-methoxy-aniline, 5,6-dichloro-2-methoxy-aniline, 3,4,6-trichloro-2-methoxy-aniline, 3,4,5-trichloro-2-methoxy-aniline, 3,4,5,6-tetrachloro-2-methoxy-aniline, 4,5-dichloro-3-methoxy-aniline, 5,6-dichloro-3-methoxy-aniline, 2,5-dichloro-3-methoxy-aniline, 4,5,6-trichloro-3-methoxy-aniline, 2,4,5,6-tetrachloro-3-methoxy-aniline, 2,3-dichloro-4-methoxy-aniline, 2,5-dichloro-4-methoxy-aniline, 2,3,6-trichloro-4-methoxy-aniline, 2,3,5-trichloro-4-methoxy-aniline, 2,3,5,6-tetrachloro-4-methoxy-aniline, 4,5-dichloro-2-phenoxy-aniline, 3,4,5,6-tetrachloro-2-phenoxy-aniline, 2,4,5,6-tetrachloro-3-phenoxy-aniline, 2,5-dichloro-4-phenoxy-aniline and 2,3,5,6-tetrachloro-4-phenoxy-aniline.

The process according to the invention is carried out in the presence of hydrogen iodide and/or a compound yielding hydrogen iodide under the reaction conditions of the process according to the invention and in the simultaneous presence of optionally substituted phenols, over a catalyst of noble metals in elementary or bonded form and, if appropriate, in the presence of an inert organic solvent and/or diluent and/or water.

The hydrogen iodide can be employed in the process according to the invention as a gas or in the form of an approximately 0.1 to 65% strength by weight, preferably a 10 to 60% strength by weight, aqueous solution. For this process, the hydrogen iodide can be produced in situ from elementary iodine or from iodine compounds which yield hydrogen iodide under the reaction conditions of the process according to the invention.

Examples of suitable inorganic or organic compounds which yield hydrogen iodide are: iodine, sodium iodide, potassium iodide, $KI_3$ solution, iodine chloride, iodic acid and the salts thereof, iodoalkanes, such as iodomethane, iodoethane, 1-iodopropane and 2-iodopropane, aromatic iodine compounds, such as 2-iodophenol and 4-iodophenol, preferably iodine, sodium iodide, potassium iodide, 2-iodopropane, 2-iodophenol, 4-iodophenol and iodine chloride.

In general, the hydrogen iodide is employed according to the process according to the invention in quantities of 0.01 to 20% by weight, preferably 0.1 to 10% by weight, relative to the amount by weight of the aniline to be dehalogenated. If iodine or a compound yielding hydrogen iodide is used in the process according to the invention, they are customarily employed in quantities from 0.01 to 20% by weight, preferably from 0.1 to 10% by weight, relative to the amount by weight of the aniline to be dehalogenated.

The optionally substituted phenols are preferably employed undiluted in the process according to the invention. However, it is also possible to employ the phenols in solution in, or diluted with, an organic solvent and/or diluent, which is inert under the reaction conditions, or in water.

Suitable optionally substituted phenols are those which are mono- or poly-substituted by alkyl groups with up to 4 carbon atoms or by halogen, preferably by iodine.

Examples which may be mentioned are: phenol, o-, m- or p-cresol, 2,3-, 2,4-, 2,5-, 2,6- or 3,5-xylenol, 2- and 4-iodophenol. The optionally substituted phenols can be employed in the process according to the invention individually as well as in mixtures with one another, for example m-/p-cresol mixtures.

The amount of optionally substituted phenols to be used in the process according to the invention can be varied within wide ranges. Usually, 1 to 90% by weight, preferably 30 to 70% by weight, of the optionally substituted phenols, relative to the amount of the reaction mixture, is employed in the process according to the invention.

Noble metals which may be mentioned are the elements of the 8th Group of the Periodic System of the elements (Mendeleyev), such as ruthenium, rhodium, palladium, osmium, iridium and platinum, preferably ruthenium, platinum and palladium.

The oxides, sulphides and/or polysulphides can be employed, for example, as the bonded forms of the noble metals.

The catalysts according to the process according to the invention can also be employed on carrier materials. Suitable for this purpose are all carrier materials which are in themselves known and are inert to water and acids. Such materials which may be mentioned are barium sulphate and active charcoal, preferably active charcoal.

The preparation of the noble metal catalyst on a carrier material can be effected in a manner which is in itself known. For example, the carrier material is suspended in the aqueous solution of the noble metal and the noble metal is then precipitated onto the carrier material by addition of a reducing agent, such as hydrogen or hydrazine.

It is particularly advantageous in the continuous operation of the process according to the invention to arrange the noble metal catalyst, on a carrier material in the reaction space, as a fixed-bed catalyst or fluidized-bed catalyst.

The catalysts, which are employed for the operation of the process according to the invention, retain their activity and their selectivity over a long period of time, even when used in several repetitions of the process or in continuous operation of the process according to the invention, and give constantly high yields.

The quantity of catalyst, which is employed in the operation of the process according to the invention, is, in general, 0.1 to 2% by weight, preferably 1 to 1.5% by weight, relative to the aniline used as starting material. When a catalyst applied on a carrier is used, 1 to 20% by weight, preferably 10 to 15% by weight, relative to the starting material, is customarily employed.

The process according to the invention is carried out, if appropriate, in the presence of inert organic solvents and/or diluents and/or in the presence of water. Methyl alcohol, ethyl alcohol, benzene, chlorobenzene, o-dichlorobenzene, toluene and xylene, preferably toluene, are mentioned as examples of inert organic solvents and/or diluents.

In general, the process according to the invention is carried out in an acid medium. The acid medium can be produced either by means of the hydrogen halide formed during the reaction or by means of the hydrogen iodide introduced.

In the presence of water, the process according to the invention is carried out, in general, at a pH value of less than 4, preferably less than 1.

In order to adjust the pH value of the acid medium to <1, a small amount of hydrogen halide can be added to the mixture before the beginning of the reaction. The amount of hydrogen halide added is preferably kept very low, in order to avoid an increased amount, formed of necessity during the reaction, of hydrogen halide or salts thereof in the working-up process. Iodine in phenolic solution, which forms hydrogen iodide under the reaction conditions, or hydrogen iodide itself or one of the iodine compounds already mentioned, which also yield hydrogen iodide under the reaction conditions and thus produce an acid medium, is preferably employed.

The process according to the invention can be illustrated by means of the following equation of the reaction for the dechlorination of pentachloroaniline to give 3,5-dichloroaniline:

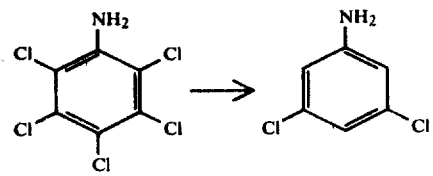

According to the process according to the invention, it is possible, for example, not only to use pure tetrachloroanilines or pentachloroaniline as starting materials, but also to use mixtures of tetrachloroanilines and pentachloroaniline, as produced in the industrial production of tetrachlorobenzene by nitration and catalytic reduction of the nitro group.

Furthermore, it is possible to employ the corresponding nitrochloro compounds instead of the chlorinated anilines as starting material, and to carry out the reduction of the nitro group and the hydrogenating dehalogenation process in a one-pot reaction.

In general, the process according to the invention is carried out in such a manner that the starting material, the phenol, if appropriate a solvent or diluent, a catalyst and hydrogen iodide or a compound which yields hydrogen iodide under the reaction conditions of the process are initially introduced into an acid resistant autoclave, for example, an autoclave made of enamel or tantalum, and, after closing the autoclave, the air is displaced by nitrogen and the nitrogen is then displaced by hydrogen.

To carry out the reaction, the hydrogen is introduced into the reaction mixture in gaseous form. In general, the hydrogen pressure is from 10 to 100 bars, preferably 15 to 60 bars, particularly preferably 20 to 50 bars. Thus, the process can be carried out at a pressure of less than 60 bars.

The process according to the invention is carried out, in general, at a temperature of from 100° to 250° C., preferably at 120° to 200° C., particularly preferably at 140° to 190° C. The process can be carried out at a temperature less than 200° C.

The duration of the reaction depends, inter alia, on the reaction temperature employed and the hydrogen pressure employed, and is about 2 hours at 170° C.

After the reaction has ended, the mixture can be worked up in a manner which is in itself known. For example, when water is used as the solvent and/or diluent, the catalyst can be separated off by filtration of the hot mixture under suction. The m-halogen-substituted anilines can then be liberated by addition of, for example, alkali metal hydroxide solution, and can be extracted with a water-immiscible solvent, for example methylene chloride or toluene. The phenol remains in this case as an alkali phenolate in solution. The halogenoanilines can be obtained from the solvent, for example by distillation.

When a water-immiscible solvent and/or diluent is employed, the 3-halogenoanilines or the 3,5-dihalogenoanilines can be liberated by addition of aqueous alkali metal hydroxide. The organic solvent can then be separated off and the m-halogen-substituted aniline can be isolated from the solvent, for example by distillation.

A particular form of the working up process can consist of the following: for example, after diluting the reaction mixture with water, filtering off the catalyst under suction and neutralizing the filtrate, for example with sodium hydroxide solution, the organic phase is separated off, if necessary with the aid of an organic solvent, such as toluene, and the particular halogen-substituted aniline is obtained by distillation.

The iodine can be reclaimed by known methods, such as by oxidation of the iodide with chlorine and extraction of the iodine formed thereby with a suitable organic solvent.

In a particular embodiment of the process according to the invention, the iodine can be reclaimed by oxidizing the aqueous phase containing iodide, for example with hydrogen peroxide in the presence of a little acid, preferably in the presence of hydrochloric acid, taking up the iodine thereby formed in phenol and using this iodine solution in a further reaction cycle.

The process according to the invention can be carried out discontinuously as well as continuously.

The process according to the invention has the advantage that a selective dechlorination giving a high yield can be carried out under mild reaction conditions and with high concentrations of starting material, without supplementary addition of salts, such as alkali metal chlorides or alkaline earth metal chlorides, or of acids, such as hydrochloric acid, or of heavy metal salts, such as, for example, those mentioned in the European Patent Application No. 0,015,220.

A further advantage of the process according to the invention is that chloroaniline mixtures which are difficult to separate can also be used as starting material, which mixtures, in addition to the polychloroanilines which are substituted by chlorine in the m-position to the amino group, contain further chloroanilines or polychloroanilines in which there is no chlorine in the m-position to the amino group. These compounds are dechlorinated according to the process according to the invention to give aniline, which may be easily separated off by distillation. In contrast, the separation of a polychloroaniline mixture is inconvenient and tedious.

Further, a mixture of tetrachloroanilines and pentachloroaniline, as obtainable from an industrially produced tetrachlorobenzene mixture by nitration and catalytic reduction of the nitro group, can be selectively dehalogenated, according to the process according to the invention, to give 3,5-dichloroaniline in high yield.

Furthermore, it is possible to employ the corresponding chloronitro compounds as starting material, instead of the chlorinated anilines, and to carry out the reduction of the nitro group and the hydrogenating dehalogenation in a one-pot reaction.

It must be further regarded as advantageous that the phenol employed in the dehalogenation reaction is not converted by hydrogenation of the nucleus to cyclohexanol or cyclohexanone, under the reaction conditions mentioned and in the presence of noble metal catalysts and hydrogen. The phenol can therefore be reclaimed, in each case by a simple separation operation, such as extraction or distillation, and used again. In addition, the phenol is an excellent medium for the recycling of the iodine reclaimed in the reaction according to the invention, thus allowing the process according to the invention to be organised in an even more economical way. The use of optionally substituted phenols in the process according to the invention has a further substantial advantage in that the compound to be dehalogenated can be employed in very high concentration, whilst, at the same time, a very low concentration of noble metal catalyst can be used. Particularly high space-time yields, hitherto not achieved, are thereby obtained.

The following may be mentioned as examples of anilines of the formula (II), meta-substituted by halogen, which can be prepared according to the process according to the invention: 3-chloro-aniline, 3,5-dichloro-aniline, 3-chloro-5-iodo-aniline, 5-chloro-2-methyl-aniline, 5-chloro-3-methyl-aniline, 3-chloro-4-methyl-aniline, 3,5-dichloro-4-methyl-aniline, 5-chloro-3,4-dimethyl-aniline, 3-chloro-4-ethyl-aniline, 3-chloro-2-benzyl-aniline, 4,4'-diamino-2,6,2',6'-tetrachloro-diphenyl, 3-chloro-2-methoxy-aniline, 5-chloro-2-methoxy-aniline, 3,5-dichloro-2-methoxy-aniline, 3-chloro-4-methoxy-aniline, 5-chloro-3-methoxy-aniline, 3,5-dichloro-4-methoxy-aniline, 3-chloro-2-phenoxy-aniline, 3,5-dichloro-2-phenoxy-aniline and 3,5-dichloro-4-phenoxy-aniline.

The 3-chloroanilines or 3,5-dichloroanilines which can be obtained according to the process according to the invention are known intermediate products and can be used in the preparation of plant protection agents (German No. 1,034,912, German Offenlegungsschrift No. 2,021,327, German Offenlegungsschrift No. 1,812,206, German Offenlegungsschrift No. 1,958,183, U.S. Pat. Nos. 2,906,614, 2,655,445 and 3,652,737).

The following examples are intended to illustrate the process according to the invention.

EXAMPLE 1

200 parts of phenol, 197 parts of 2,3,5,6-tetrachloroaniline, 20 parts of platinum-on-charcoal catalyst (3.7% strength) and 15 parts of aqueous hydroiodic acid (57% strength) are dehalogenated with hydrogen in a tantalum autoclave (0.85 l) during the course of 3.5 hours, whilst stirring, under a maximum pressure of 50 bars and at 155° C. After cooling of the reaction vessel and after releasing the pressure, the reaction mixture is diluted with 500 parts by volume of water, made alkaline with concentrated sodium hydroxide solution, mixed with toluene and separated from the platinum-on-charcoal catalyst by filtration under suction. The organic phase obtained by layer separation is freed from the solvent by distillation. 99.3% strength, 3,5-dichloroaniline is obtained in a yield of 97%, with complete conversion of 2,3,5,6-tetrachloroaniline, by distillation over a simple distillation bridge.

EXAMPLE 2

200 parts of phenol, 131 parts of 2,3,5,6-tetrachloroaniline, 10 parts of aqueous hydroiodic acid (57% strength) and 20 parts of ruthenium-on-charcoal catalyst (5% strength) are dehalogenated in a tantalum autoclave in the course of 4 hours, whilst stirring, at a temperature of 165° C. and with hydrogen under a maximum pressure of 50 bars. After the usual working up process, 90.5 parts of 3,5-dichloroaniline (99.1% strength) are obtained; yield: 98% of theory.

EXAMPLE 3

200 parts of phenol and 131 parts of a mixture of 2,3,4,5- and 2,3,5,6-tetrachloroaniline and pentachloroaniline in the ratio in % by weight of about 38:60:2 are mixed with 20 parts of ruthenium-on-charcoal catalyst (5% strength) and 10 parts of aqueous hydroiodic acid (57% strength) and the mixture is dehalogenated in a tantalum autoclave (0.85 l) at a temperature of 165° C. with hydrogen under a maximum pressure of 50 bars, in the course of 10 hours. After working up according to the method described in Example 1, 91.5 parts of 3,5-dichloroaniline (98.1% strength), with a content of 0.6% of 3-chloro-aniline which can be separated off by distillation, is obtained. Yield: 98% of theory.

EXAMPLE 4

If Example 2 is carried out using 5 parts of Pd-on-charcoal catalyst (5% strength) instead of the ruthenium-on-charcoal catalyst, 88.5 parts of 99% strength 3,5-dichloroaniline are obtained after a reaction time of 3 hours at 165° C. and after the usual working up; yield: 95% of theory.

EXAMPLE 5

200 parts of phenol, 131 parts of a tetrachloroaniline/pentachloroaniline mixture corresponding to the composition mentioned in Example 3, 1 part of ruthenium-on-charcoal catalyst (5% strength) which has already been used for 10 previous similar experiments, and 12 parts of aqueous hydrochloric acid (57% strength) are reacted in a tantalum autoclave, during the course of 3.5 hours at 165° C., whilst stirring, at a hydrogen pressure of 50 bars. After the usual working up, 90 parts of 99% strength 3,5-dichloroaniline are isolated. Yield: 97% of theory.

EXAMPLE 6

131 parts of tetrachloroaniline/pentachloroaniline mixture corresponding to the data in Example 3, 200 parts of phenol, 5.7 parts of iodine and 33 parts of a 5% strength ruthenium-on-charcoal catalyst which is moist with water (23 parts dry) are brought to reaction in a tantalum autoclave, whilst stirring, during the course of 4 hours, at 165° C. and under a maximum hydrogen pressure of 50 bars. After the usual working up, 87 parts of 98% strength 3,5-dichloroaniline are obtained (93% yield).

EXAMPLE 7

If the reaction is repeated according to Example 3, but, instead of the aqueous hydroiodic acid, 10 parts of 2-iodopropane are employed, 89 parts of 3,5-dichloroaniline are obtained after working up. Yield: 97% of theory.

EXAMPLE 8

131 parts of a tetrachloroaniline/pentachloroaniline mixture, 200 parts of phenol and 10 parts of 2-iodophenol are reacted in the presence of 12.5 parts of ruthenium-on-charcoal catalyst (5%) in a tantalum autoclave with hydrogen under a pressure of from 29 to 50 bars at a maximum temperature of 165° C., during the course of 8 hours, whilst stirring. 87.5 parts of 3,5-dichloroaniline are obtained after working up the reaction mixture. Yield: 95% of theory.

EXAMPLE 9

55.5 parts of 4-bromo-3-chloro-5-iodoaniline, 250 parts of phenol, 8 parts of hydroiodic acid (57% strength) and 15 parts of ruthenium-on-charcoal catalyst (5% strength) are reacted with hydrogen under a pressure of 23 to 47 bars and at 145° C., during the course of 2 hours, whilst stirring. After the usual working up, 38 parts of 3-chloro-5-iodo-aniline are obtained. Yield: 90% of theory.

EXAMPLE 10

163 parts of 2,5-dichloroaniline (99.8% strength), 250 parts of phenol, 14 parts of aqueous hydroiodic acid (57% strength) and 23 parts of ruthenium-on-charcoal catalyst (5% strength) are stirred in a tantalum autoclave for 6 hours at 190° C. under a maximum hydrogen pressure of 50 bars. After working up the reaction mixture analogously to Example 1, 119 parts of crude 3-chloroaniline are obtained, which, according to gas chromatographic analysis, still contains 0.2% of phenol and 3.5% of 2,5-dichloroaniline (starting material), and which can be purified by distillation.

EXAMPLE 11

105 parts of 2,3,5,6-tetrachloro-4-methylaniline (99.4% strength) in 250 parts of phenol in the presence of 9 parts of hydroiodic acid (57% strength) and 23 parts of a 5% strength ruthenium-on-charcoal catalyst are reacted in a tantalum autoclave for 6.5 hours at 165° C. under a hydrogen pressure of 50 bars, whilst stirring. After working up analogously to Example 1, 73.5 parts of 3,5-dichloro-4-methyl-aniline are obtained; melting point 55.5 to 56.5° C.; boiling point 147° to 150° C./14 mbars; 98.6% strength. The yield is 96.2% of theory.

EXAMPLE 12

100 parts of pentachloroaniline, 200 parts of phenol, 7 parts of hydroiodic acid (57% strength) and 23 parts of ruthenium-on-charcoal catalyst (5% strength) are stirred in a tantalum autoclave for 9 hours at 165° C. with hydrogen under a maximum pressure of 50 bars. After working up analogously to the method described in Example 1, 59 parts of 3,5-dichloroaniline are obtained. The yield is 92.5% of theory.

EXAMPLE 13

164 parts of 2,3-dichloroaniline (99.2% strength), 250 parts of phenol, 14 parts of hydroiodic acid (57% strength) and 23 parts of ruthenium-on-charcoal catalyst (5% strength) are stirred for 12 hours with hydrogen under a pressure of 50 bars at 180° C. After working up the reaction mixture according to the method described in Example 1, 121 parts of crude 3-chloroaniline (96.4% strength) and also 3.1% of 2,3-dichloroaniline are obtained. Pure 3-chloroaniline is obtained by distillation; yield 91.8% of theory.

EXAMPLE 14

61.5 parts of 2,4,5-trichloroaniline, 200 parts of phenol, 10 parts of aqueous hydroiodic acid (57% strength) and 23 parts of ruthenium-on-charcoal catalyst (5% strength) are stirred in a tantalum autoclave for 4.5 hours at 180° C. with hydrogen under a maximum pressure of 50 bars. After working up, a product is obtained which, according to gas chromatographic analysis, contains 0.7% of aniline, 90.1% of 3-chloroaniline and 8.2% of 2,5-dichloroaniline, and which can be purified by distillation. Yield: 88% of theory.

EXAMPLE 15

200 parts of phenol, 5.7 parts of iodine, 197 parts of a tetrachloroaniline/pentachloroaniline mixture according to the data in Example 3, and 20 parts of ruthenium-on-charcoal catalyst (5% strength) are subjected to a hydrogenating dehalogenation in a tantalum autoclave at 175° C. with hydrogen under a maximum pressure of 50 bars. In the working up process, the hot mixture is dissolved in 450 parts by volume of water at 100° C., the catalyst is separated off through a suction filter and the filtrate is neutralised with sodium hydroxide solution. 3,5-Dichloroaniline and phenol are separated off from the water phase with the aid of toluene, and the organic solution is distilled. After distilling off toluene and water, the phenol is separated off from the 3,5-dichloroaniline by distillation and can be used again. The crude 3,5-dichloroaniline which remains is purified by distillation over a simple distillation bridge. 132 parts of 98% strength 3,5-dichloroaniline is obtained; yield 94% of theory.

In order to reclaim the iodine, 40 parts of phenol are added to the water phase, the mixture is acidified with hydrochloric acid and the iodine is oxidised with aqueous 35% strength hydrogen peroxide solution (approximately 4 parts). The phenolic iodine solution is separated off and is used again in a further reaction cycle. After steam treatment to remove remaining phenol, the water phase is free from iodine.

EXAMPLE 16

131 parts of a mixture of tetrachloroaniline and pentachloroaniline, corresponding to the composition given in Example 3, 200 parts of phenol and 9 parts of sodium iodide are reacted in the presence of 22 parts of a ruthenium-on-charcoal catalyst (5% strength) which is moist with water and has already been used for 6 similar reaction cycles, corresponding to 15 parts of dry catalyst, with hydrogen at 165° C. under a pressure of 40 to a maximum of 50 bars, during the course of 8 hours. After the usual working up, 91.5 parts of 3,5-dichloroaniline are obtained, with complete conversion of the starting material. Yield: 98% of theory.

EXAMPLE 17

150 parts of a mixture of tetrachloronitrobenzene and pentachloronitrobenzene, the composition of which corresponds to that of the polychloroaniline mixture of Example 3, 200 parts of phenol and 10 parts of aqueous hydroiodic acid (57% strength) are reacted with hydrogen in the presence of 20 parts of ruthenium-on-charcoal catalyst (5% strength), starting at approximately 60° C. to a maximum of 165° C. under a pressure of 20 bars, at the beginning, to a maximum of 50 bars, during the course of 10 hours. After working up, 84.5 parts of 3,5-dichloroaniline are obtained. Yield 92% of theory.

EXAMPLE 18

46.2 parts of 2,3,4,5-tetrachloroaniline (0.2 mol), 154 parts of phenol, 4 parts of hydrogen iodide (57% strength aqueous solution) and 3 parts of a 10% strength platinum-on-charcoal catalyst are mixed together in a 0.85 l tantalum autoclave and are reacted, whilst stirring, at 160° C. with hydrogen under a total pressure of 18 bars maximum, during the course of 3 hours. After the usual working up, 3,5-dichloroaniline is obtained in a yield of 97% of theory, with complete conversion of tetrachloroaniline.

EXAMPLE 19

131 parts of a tetrachloroaniline/pentachloroaniline mixture (see Example 3), 200 parts of o-cresol, 10 parts of aqueous hydroiodic acid (57% strength) and 10 parts of ruthenium-on-charcoal catalyst (5% strength) are initially introduced into a tantalum autoclave (0.85 l) and are brought to reaction with hydrogen at 165° C. under a pressure of 45–50 bars, during the course of 5 hours, whilst stirring. After working up the mixture, 87.5 parts of 3,5-dichloroaniline are obtained, 95% of theory.

Comparison Example (to Example 1 of the European Patent Application No. 0,015,219)

131 parts of 2,3,5,6-tetrachloroaniline, 135 parts of 4 N hydrochloric acid, 5.5 parts of palladium-on-charcoal catalyst (10% strength) and 6 ml of 7.6 molar potassium iodide solution (=7.45 parts of potassium iodide) are heated in a tantalum autoclave (0.85 l), whilst stirring, with hydrogen under a pressure of 50 bars at 165° C. for 3 hours 15 minutes. After working up, 120.5 parts of a product mixture are obtained, which consists only to 9.6% of 3,5-dichloroaniline, 69% of the tetrachloroaniline employed has not reacted and 20% consists of trichloroaniline.

This example proves the superiority of the process according to the invention (see Example 1) over the procedure according to Example 1 of the European Patent Application.

What is claimed is:

1. A process for the preparation of an m-halogen-substituted aniline which comprises contacting an aniline of the formula

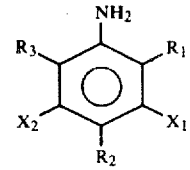

wherein
X₁ and X₂ are identical or different and represent chlorine, bromine, iodine, hydrogen or an optionally substituted alkyl, aryl, aralkyl, alkoxy or aralkoxy radical with the proviso that at least one of $X_1$ and $X_2$ is chlorine, bromine or iodine;
R₁, R₂ and R₃ are identical or different and represent chlorine, bromine, iodine, hydrogen or an optionally substituted alkyl, aryl, aralkyl, alkoxy or aryloxy radical, at least one of the radicals R₁, R₂ or R₃ representing chlorine, bromine or iodine with hydrogen in an acid medium in the presence of a nobel metal, the process being carried out in the presence of hydrogen iodide or a compound which under the process conditions yields hydrogen iodide and in the presence of an optionally substituted phenol.

2. A process according to claim 1, wherein the hydrogen iodide is supplied by iodine, sodium iodide, potassium iodide, 2-iodopropane, 2-iodophenol, 4-iodophenol and/or iodine chloride.

3. A process according to claim 1, wherein the hydrogen iodide or a compound which under the process conditions yields hydrogen iodide is present in the reaction mixture in an amount from 0.01 to 20% by weight, based upon the weight the aniline.

4. A process according to claim 1, wherein the optionally substituted phenol is phenol, a cresol, a xylenol and/or an iodophenol.

5. A process according to claim 1, wherein said optionally substituted phenol is present in the reaction mixture in an amount from 1 to 90% by weight, based upon the total weight of the reaction mixture.

6. A process according to claim 1, wherein the optionally substituted phenol is present in an amount from 30 to 70% by weight, based upon the total weight of the reaction mixture.

7. A process according to claim 1, wherein the process is carried out at a temperature of from 100° to 250° C.

8. A process according to claim 7, wherein the process is carried out at a temperature below 200° C.

9. A process according to claim 1, wherein the process is carried out at a pressure of 10 to 100 bars.

10. A process according to claim 9, wherein the process is carried out at a pressure of less than 60 bars.

11. A process according to claim 9, wherein the process is carried out at a pressure of from 20 to 50 bars.

12. A process according to claim 1, wherein following the reaction, the reaction mixture is diluted with water, the catalyst is filtered off and the filtrate is neutralized, the organic phase is separated off leaving an aqueous phase, the aqueous phase is oxidized with hydrogen peroxide in the presence of an acid, and iodine formed is taken up in phenol and the resultant phenolic solution is recycled to the reaction of the chlorinated aniline with hydrogen in the acidic medium.

13. A process according to claim 1, wherein the process is carried out employing a reaction mixture whose pH is less than 4.

14. A process according to claim 1, wherein the process is carried out in a reaction mixture whose pH is less than 1.

15. A process according to claim 1, wherein the catalyst is disposed on an inert support.

16. A process according to claim 1, wherein the process is carried out in the presence of an inert organic solvent or diluent.

17. A process according to claim 1, wherein the process is carried out in the presence of water.

18. A process according to claim 1, wherein the nobel metal is in elementary form.

19. A process according to claim 1, wherein the nobel metal is in the form of a compound.

20. A process according to claim 1 wherein said optionally substituted phenol is present in the reaction mixture in an amount from 30 to 90 percent by weight based upon the total weight of the reaction mixture.

21. A process according to claim 20 wherein both $X_1$ and $X_2$ are independently chlorine, bromine or iodine.

22. A process according to claim 21 wherein said aniline is 2,3,5,6-tetrachloroaniline.

23. A process according to claim 21 wherein said aniline is pentachloroaniline.

24. A process according to claim 21 wherein said aniline is 2,3,5,6-tetrachloro-4-methylaniline.

25. A process according to claim 21 wherein each of the 2, 3, 5 and 6 positions of said aniline are occupied by chlorine, bromine or iodine.

* * * * *